(12) United States Patent
Shao et al.

(10) Patent No.: US 11,241,221 B2
(45) Date of Patent: Feb. 8, 2022

(54) METHOD FOR PROCESSING MORPHOLOGY INFORMATION AND ELASTICITY INFORMATION OF TISSUE AND DEVICE FOR ELASTICITY DETECTION

(71) Applicant: WUXI HISKY MEDICAL TECHNOLOGIES CO., LTD., Wuxi (CN)

(72) Inventors: Jinhua Shao, Wuxi (CN); Jin Sun, Wuxi (CN); Houli Duan, Wuxi (CN)

(73) Assignee: WUXI HISKY MEDICAL TECHNOLOGIES CO., LTD., Wuxi (CN)

( * ) Notice: Subject to any disclaimer, the term of this patent is extended or adjusted under 35 U.S.C. 154(b) by 321 days.

(21) Appl. No.: 15/497,110

(22) Filed: Apr. 25, 2017

(65) Prior Publication Data

US 2017/0224316 A1    Aug. 10, 2017

Related U.S. Application Data

(63) Continuation of application No. PCT/CN2015/081941, filed on Jun. 19, 2015.

(30) Foreign Application Priority Data

Apr. 20, 2015   (CN) .......................... 201510189246.2

(51) Int. Cl.
| | | |
|---|---|---|
| *A61B 10/02* | (2006.01) | |
| *A61B 8/00* | (2006.01) | |
| *A61B 8/08* | (2006.01) | |

(52) U.S. Cl.
CPC ................ *A61B 10/02* (2013.01); *A61B 8/08* (2013.01); *A61B 8/0841* (2013.01);
(Continued)

(58) Field of Classification Search
CPC ..... A61B 8/0841; A61B 8/5253; A61B 8/485; A61B 8/4477; A61B 8/5223; A61B 8/4254; A61B 8/5246
See application file for complete search history.

(56) References Cited

U.S. PATENT DOCUMENTS

| | | | |
|---|---|---|---|
| 2010/0049044 A1 | 2/2010 | Bircher | |
| 2011/0301451 A1* | 12/2011 | Rohling | ................... A61B 8/00 600/424 |

(Continued)

FOREIGN PATENT DOCUMENTS

| | | |
|---|---|---|
| CN | 102599938 A | 7/2012 |
| CN | 103124523 A | 5/2013 |

(Continued)

OTHER PUBLICATIONS

Guibal et al. "Evaluation of Shearwave Elastography for the Characterization of Focal Liver Lesions on Ultrasound". Eur Radiol 23: 1138-1149 (2013) (Year: 2013).*

(Continued)

*Primary Examiner* — Keith M Raymond
*Assistant Examiner* — Milton Truong
(74) *Attorney, Agent, or Firm* — J.C. Patents (57) ABSTRACT

Provided is a device for elasticity detection, comprising a processor (1), an imaging device (2), an ultrasonic transducer (3) and a puncturing device (4). The ultrasonic transducer (3) is connected to the processor (1) and is configured to detect and obtain morphology characteristic information and elasticity characteristic information of a tissue. The imaging device (2) is connected to the processor (1) and is configured to obtain a morphology image and an elasticity image of the tissue according to the morphology characteristic information and the elasticity characteristic information, respectively, under the control of the processor (1), and merge and display the elasticity image in the morphology (Continued)

image. The puncturing device (4) is connected to the processor (1) and is configured to determine a puncture position according to guidance of the merged image and perform a puncturing and sampling on the tissue.

14 Claims, 4 Drawing Sheets

(52) U.S. Cl.
CPC .......... *A61B 8/4477* (2013.01); *A61B 8/485* (2013.01); *A61B 8/5223* (2013.01); *A61B 8/5246* (2013.01); *A61B 8/5253* (2013.01); *A61B 8/4254* (2013.01); *A61B 8/4281* (2013.01); *A61B 8/461* (2013.01)

(56) References Cited

U.S. PATENT DOCUMENTS

| | | | | |
|---|---|---|---|---|
| 2013/0096430 A1* | 4/2013 | Yoshiara | .............. | A61B 8/0841 600/438 |
| 2015/0045668 A1* | 2/2015 | Smith | .................. | A61B 8/4455 600/447 |
| 2015/0133788 A1* | 5/2015 | Mauldin, Jr | ......... | A61B 8/5253 600/444 |
| 2016/0143622 A1* | 5/2016 | Xie | ...................... | A61B 8/4245 600/424 |

FOREIGN PATENT DOCUMENTS

| | | |
|---|---|---|
| CN | 202917083 U | 5/2013 |
| CN | 103179907 A | 6/2013 |
| CN | 103402439 A | 11/2013 |
| CN | 103578099 A | 2/2014 |
| CN | 104224233 A | 12/2014 |
| CN | 204600529 U | 9/2015 |
| EA | 200300605 A1 | 12/2003 |
| EA | 005391 B1 | 2/2005 |
| JP | 2004-89362 A | 3/2004 |
| JP | 2004-141505 A | 5/2004 |
| JP | 4498451 B2 | 4/2010 |
| JP | 4711775 B2 | 4/2011 |
| JP | 2013-27512 A | 2/2013 |
| JP | 2013-240369 A | 12/2013 |
| RU | 2012112934 A | 10/2013 |
| RU | 2535410 C1 | 12/2014 |
| WO | WO 2005/010711 A2 | 2/2005 |
| WO | WO2006/054635 A1 | 5/2006 |
| WO | WO 2012/037181 A1 | 3/2012 |
| WO | WO 2014/082483 A1 | 6/2014 |
| WO | WO 2014/162966 A1 | 10/2014 |
| WO | WO 2014/207605 A1 | 12/2014 |

OTHER PUBLICATIONS

Park et al. "Strain Elastography of Abnormal Axillary Nodes in Breast Cancer Patients Does Not Improve Diagnostic Accuracy Compared With Conventional Ultrasound Alone". AJR 203:1371-1378 (2014) (Year: 2014).*
The Japanese Examination Report of corresponding Japan patent application No. 2017-554440, dated Dec. 5, 2018.
The Japanese Examination Report of corresponding Japan patent application No. 2017-554440, dated Jul. 30, 2018.
International Search Report of corresponding International PCT Application No. PCT/CN2015/081941, dated Jan. 5, 2016.
Chinese First Examination Report of corresponding Chinese patent Application No. 201510189246.2, dated Sep. 26, 2016.
Yaseen, Mohammad A et al., "Optoacoustic imaging of the prostate: development toward imag-guided biopsy" Journal of Biomedical Optics; vol. 15, No. 2; (Mar./Apr. 2010); Doi: 10.1117/1.3333548; p. 021310-1-021310-8.
The Russian Examination Report of corresponding Russian Federation patent application No. 2017140047/14(069593), dated Oct. 24, 2018.
The Chinese Second Examination Report of corresponding Chinese patent application No. 201510189246.2, dated May 3, 2017.
The extended European Search Report of corresponding European application No. 15889607.6-1124/3287078, dated Aug. 21, 2018.
The first Office Action of the parallel IN application.
"Breast Disease Clinical Application of US elastography for diagnosis", Radiology: vol. 239: No. 2—May 2006.

* cited by examiner

METHOD FOR PROCESSING MORPHOLOGY INFORMATION AND ELASTICITY INFORMATION OF TISSUE AND DEVICE FOR ELASTICITY DETECTION

CROSS-REFERENCE TO RELATED APPLICATIONS

This application is a continuation of International Application No. PCT/CN2015/081941, filed on Jun. 19, 2015, which claims the priority benefit of China Patent Application 201510189246.2, filed on Apr. 20, 2015. The contents of the above identified applications are incorporated herein by reference in their entireties.

TECHNICAL FIELD

The present invention relates to the technical field of data processing, and in particular to a method for processing morphology information and elasticity information of a tissue and a device for elasticity detection.

BACKGROUND

Performing an analysis on the morphological features of organs and tissues can provide ancillary support for doctors to diagnose and treat diseases. For example, tissue aspiration biopsy is a method widely used in clinical practice, where a tissue sample is obtained by means of a biopsy needle, and is sectioned to read for obtaining a pathological section of the tissue, to determine the extent of pathological change of the tissue, and to ultimately provide ancillary support for determining the pathogeny and focus. In general, in order to obtain a more accurate location of a tissue specimen, the aspiration biopsy is usually performed in conjunction with an image guiding method for a tissue and structure.

Traditional medical imaging methods such as CT, ultrasound or the like obtain two-dimensional or three-dimensional structural morphology information through different principles. If a tissue has a lesion, then its structural morphology will generally change. Therefore, position of the puncture tissue is guided and indicated by an image of the structural morphology, which is of great significance in clinical practice.

Tissue aspiration biopsy is the gold standard for diagnosis of a large amount of tissues and organs, and the existing aspiration biopsy is performed by means of an image guiding method for structure morphology of a tissue, while aspiration biopsy sampling is performed under the guidance of ultrasound and is used for pathological analysis so as to provide a basis for diagnosis and treatment through the results of pathological analysis of the tissue. However, tissue lesions sometimes do not necessarily manifest changes in morphology, especially in the early stages. Therefore, the guided puncture based on the traditional imaging information of structure morphology cannot provide an accurate guidance for some lesions, and thus it is impossible to obtain accurate information of tissue lesion and provide assistance for the final diagnosis and treatment.

SUMMARY

In order to solve the problems in the prior art, an embodiment of the present invention provides a method for processing morphology and elasticity information of a tissue, and a device for elasticity detection. The present invention may accurately locate the pathological tissue through effectively combining the morphology information of the tissue with the elasticity information of the tissue, to overcome the defect of the prior art that locating the pathological tissue only by the morphology information is unreliable.

According to a first aspect of the present invention, there is provided a method for processing morphology information and the elasticity information of a tissue, including:

obtaining a morphology image and an elasticity image of the tissue, where the morphology image includes morphology characteristic information of the tissue, and the elasticity image includes elasticity characteristic information of the tissue;

merging and displaying the elasticity image in the morphology image;

determining a puncture position according to guidance of the merged image, to perform puncturing and sampling of the tissue.

In a first possible implementation form of the first aspect, the obtaining a morphology image and an elasticity image of the tissue includes:

generating an ultrasonic wave in the tissue by a first ultrasonic transducer, obtaining morphology characteristic information according to the ultrasonic wave that is returned, and performing morphology imaging according to the morphology characteristic information to obtain a gray-scale morphology image; and generating an elasticity shear wave in the tissue by a second ultrasonic transducer, determining elasticity characteristic information generated by the tissue under action of the elasticity shear wave, and performing elasticity imaging according to the elasticity characteristic information to obtain a gray-scale or colorized elasticity image; wherein the first ultrasonic transducer and the second ultrasonic transducer are the same or different.

According to the first possible implementation form of the first aspect, in a second possible implementation form of the first aspect, the first ultrasonic transducer and the second ultrasonic transducer are different ultrasonic transducers, and the method further includes:

spatially locating the first ultrasonic transducer and the second ultrasonic transducer by a spatial location device, and performing a matching such that the first ultrasonic transducer and the second ultrasonic transducer correspond to the same scanning plane of the tissue.

According to the first or second possible implementation form of the first aspect, in a third possible implementation form of the first aspect, in the gray-scale elasticity image, different gray-scales are used to represent elasticity characteristic information corresponding to different positions of the tissue; in the colorized elasticity image, different colors are used to represent elasticity characteristic information corresponding to different positions of the tissue; and in the gray-scale morphology image, different gray-scales are used to represent morphology characteristic information corresponding to different positions of the tissue.

According to a third possible implementation form of the first aspect, in a fourth possible implementation form of the first aspect, the merging and displaying the elasticity image in the morphology image includes:

displaying in the gray-scale morphology image the elasticity characteristic information represented by different gray-scales or different colors in the gray-scale or colorized elasticity image.

According to a second aspect of the present invention, there is provided a device for elasticity detection, including:

a processor, an imaging device, an ultrasonic transducer, and a puncturing device;

the ultrasonic transducer is connected to the processor and is configured to detect and obtain morphology characteristic information and elasticity characteristic information of a tissue;

the imaging device is connected to the processor, and is configured to obtain morphology image and elasticity image of the tissue according to the morphology characteristic information and the elasticity characteristic information, respectively, under the control of the processor, and merge and display the elasticity image in the morphology image; and the puncturing device is connected to the processor, and is configured to determine a puncture position and perform a puncturing and sampling on the tissue according to the guidance of the merged image.

In a first possible implementation form of the second aspect, the number of the ultrasonic transducer is one or two.

According to the first possible implementation form of the second aspect, in a second possible implementation form of the second aspect, the ultrasonic transducer includes a first ultrasonic transducer and a second ultrasonic transducer, and the first ultrasonic transducer and the second ultrasonic transducer are respectively connected to the processor;

the first ultrasonic transducer is configured to generate an ultrasonic wave in the tissue and obtain the morphology characteristic information according to the returned ultrasonic wave;

the processor is further configured to control the imaging device to perform morphology imaging according to the morphology characteristic information, to obtain a gray-scale morphology image;

the second ultrasonic transducer is configured to generate an elasticity shear wave in the tissue and determine the elasticity characteristic information generated by the tissue under an action of the elasticity shear wave; and the processor is further configured to control the imaging device to perform an elasticity imaging according to the elasticity characteristic information, to obtain a gray-scale or colorized elasticity image.

according to the second possible implementation form of the second aspect, in a third possible implementation form of the second aspect, the device for elasticity detection further includes a spatial location device connected to the processor; and the spatial location device is configured to spatially position the first ultrasonic transducer and the second ultrasonic transducer, and perform a matching such that the first ultrasonic transducer and the second ultrasonic transducer correspond to the same scanning plane of the tissue.

According to the third possible implementation form of the second aspect, in a fourth possible implementation form of the second aspect, the spatial location device includes an electromagnetic locater or an optical locater.

According to the second, third or fourth possible implementation form of the second aspect, in a fifth possible implementation form of the second aspect, in the gray-scale elasticity image, different gray-scales represent elasticity characteristic information corresponding to different positions of the tissue; in the colorized elasticity image, different colors represent elasticity characteristic information corresponding to different positions of the tissue; and in the gray-scale morphology image, different gray-scales represent morphology characteristic information corresponding to different positions of the tissue.

According to the fifth possible implementation form of the second aspect, in a sixth possible implementation form of the second aspect, the imaging device is specifically configured to:

display in the gray-scale morphology image the elasticity characteristic information represented by the different gray-scales or the different colors in the gray-scale or colorized elasticity image.

According to the method for processing morphology information and elasticity information of the tissue and the device for elasticity detection provided by the embodiments of the present invention, elasticity characteristic information and morphology characteristic information of the tissue can be obtained through the device for elasticity detection, so as to provide a guidance for location of the puncture position by overlaying and merging of the elasticity image and the morphology image, thereby accurately locating the diseased tissue and greatly improving reliability of the aspiration biopsy.

DESCRIPTION OF EMBODIMENTS

In order to make objectives, technical solutions and advantages of the embodiments of the present invention become more apparent, the technical solutions of the embodiments of the present invention will be clearly and completely described with reference to the accompanying drawings in the embodiments of the present invention. Obviously, the described embodiments are a part rather than all of the embodiments of the present invention. All other embodiments obtained by those of ordinary skill in the art based on the embodiments of the present invention without creative labor are within the scope of the present invention.

Figure 1:
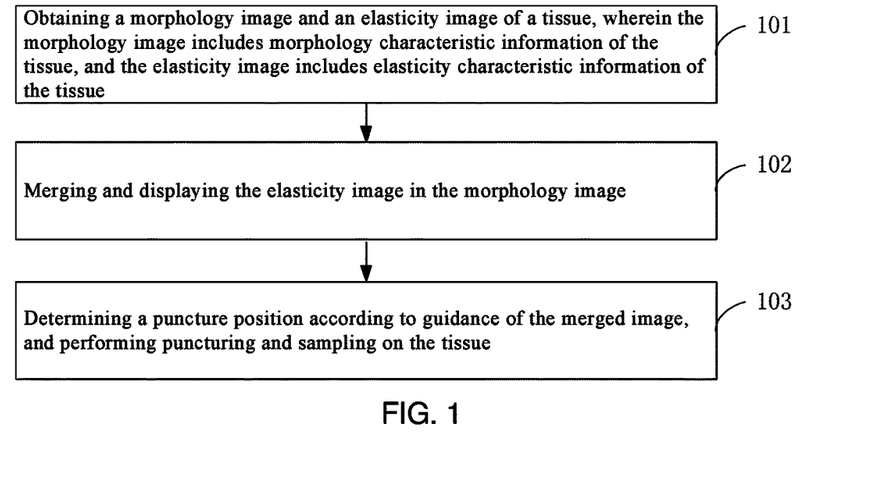
FIG. 1 is a flow chart of a first embodiment of the method for processing morphology information and elasticity information of the tissue according to the present invention.

FIG. 1 is a flow chart of the method for processing morphology information and elasticity information of the tissue according to a first embodiment of the present invention. As shown in FIG. 1, the method includes:

Step 101, obtaining a morphology image and an elasticity image of the tissue, where the morphology image includes morphology characteristic information of the tissue, and the elasticity image includes elasticity characteristic information of the tissue.

Elasticity of a biological tissue is closely related to biological characteristics of a focus, and has important reference value for diagnosis of a disease. However, traditional medical imaging modalities, including X-ray imaging, ultrasound imaging, magnetic resonance imaging (MRI) and computed tomography (CT), cannot directly provide information on the elasticity as a basic mechanical property of the tissue.

In the present embodiment, an elasticity imaging technology is employed to quantitatively detect the elasticity characteristic information of the tissue. Its basic principle is to apply an internal (including its own) or external dynamic/static/quasi-static excitation to the tissue, and the tissue will generate a response under action of elastic mechanics, biomechanics and other physical laws. Since different tissues (including normal and pathological tissues) have different elasticity coefficients (stress/strain), and thus have different strain levels after being subjected to external forces. The elasticity characteristic parameters of the tissue are obtained by processing ultrasonic signals/images obtained before and after deformation of the tissue, and then values of the elasticity characteristic parameters of the tissue are mapped into gray-scale or color images by color mapping so as to locate the lesions.

In the present embodiment, in addition to detection of the elasticity characteristic information of the tissue, a detection function of the morphology characteristic information is integrated into an existing device for tissue elasticity detection so as to jointly use elasticity information and morphology information to provide location support for the tissue aspiration biopsy. This can not only carry out normal tissue elasticity detection, but also guide aspiration biopsy of the tissue by tissue elasticity detection, which benefits integration and specialization of the device, and improvement of accuracy of the aspiration biopsy.

Specifically, in the present embodiment, the elasticity characteristic information and the morphology characteristic information of the tissue can be obtained by one or two ultrasonic transducers, and thereby obtain the morphology image, and the elasticity image of corresponding scanning plane.

For the morphology image, the ultrasonic transducer uses a piezoelectric effect to transmit an ultrasonic wave. Reflection, scattering, diffraction and other physical phenomena will occur when the ultrasonic wave propagates in the tissue. Reflected and backscattered ultrasound, i.e., the ultrasonic echo is received by the ultrasonic transducer. The ultrasonic transducer then transforms the received ultrasonic wave into electrical signals using an inverse piezoelectric effect. Afterward, the processor in the device for elasticity detection controls an imaging device to perform morphology imaging on the tissue by using a signal processing module such as AD sampling, beam forming, envelope detection and logarithmic compression, thus gray-scale imaging can be performed to obtain the gray-scale morphology images of the tissue.

For the elasticity image of the tissue, the tissue is applied an internal (including its own) or external dynamic/static/quasi-static excitation and then the tissue is deformed under the excitation, the degree of deformation is associated with the tissue's own hardness i.e., elasticity. Ultrasonic echo signals before and after the deformation are detected by the ultrasonic transducer, and if they are assumed to be S1 and S2 respectively, then there is a time shift, a frequency shift or a phase shift between the signal S1 and the signal S2. The processor in the elasticity detection device can detect the time shift/frequency shift/phase shift using signal processing methods, such as time-domain cross-correlation, spectral cross-correlation, sum of squared error, spot tracking, scale-invariant feature point tracking, dynamic programming, zero cross tracking and peak search, so as to measure the deformation of the tissue i.e., displacement, strain and other information, and then an empirical formula is used to obtain elasticity characteristic values of the tissue, the elasticity characteristic values including displacement, strain, shear wave velocity, shear wave attenuation coefficient, shear modulus, Young modulus, and the like. Finally, the processor maps the elasticity characteristic value of the tissue into gray-scale or color images by controlling the imaging device to use the color mapping, so as to obtain the gray-scale or colorized elasticity images of the tissue.

In this case, when the same ultrasonic transducer is used, since the same ultrasonic transducer corresponds to the same scanning plane of the tissue, the elasticity image matching with the morphology image can be obtained synchronously.

The case where two separate ultrasonic transducers are used, i.e., the first ultrasonic transducer and the second ultrasonic transducer, will be described in the following embodiments and thus will not be discussed here.

Step 102, merging and displaying the elasticity image in the morphology image.

The elasticity image of the tissue are merged and displayed in the morphology images. The elasticity characteristic information of the tissue is displayed in the form of color-coded gray-scale or color image by the elasticity image, with different colors or gray-scales representing the elasticity characteristic information corresponding to the different positions of the tissue, such as elasticity values. Morphology images are displayed in the form of gray-scale image, with different gray-scales representing morphology characteristic information corresponding to different positions of the tissue, such as contour marking points of the tissue. The elasticity characteristic information in the gray-scale or color image is overlaid and displayed into the morphological gray-scale image, to realize merging and displaying of the morphology characteristic information and the elasticity characteristic information.

Step 103, determining a puncture position according to guidance of the merged image, and performing puncturing and sampling on the tissue.

The advantage of merging the two images is that both the morphology characteristic information and the elasticity characteristic information can be displayed in the morphology image, so that the tissue can be displayed more accurately. For example, in the case that in the morphology image the boundaries of the tissue cannot be clearly displayed, the elasticity image can make up this; for another example, when partial volume effect causes that the morphology image cannot finely distinguish some tissues, the elasticity image can be used as auxiliary means, because the elasticity characteristic values of different tissues have different features. Furthermore, the elasticity image can display hardness distribution within the tissue, and therefore plays an important role in guiding a puncture needle into the tissue when performing a practical puncture.

It should be noted that the result of the merging is that the morphology characteristic information and the elasticity characteristic information are simultaneously displayed in the same image, that is, the morphology image and the elasticity image are merged and displayed. Also, prior to merging and displaying, it should be ensured that the locations of the tissue in the two images are matched with each other. This condition is easily met if the elasticity characteristic information and the morphology characteristic information of the tissue are obtained by the same ultrasonic transducer. If the elasticity characteristic information and the morphology feature information of the tissue are obtained by two different ultrasonic transducers, it is necessary to ensure that spatial positions and angles of the two ultrasonic transducers are relative to the same scanning plane.

In the present embodiment, by obtaining the elasticity characteristic information and the morphology characteristic information of the tissue, the morphology image and the elasticity image are obtained by imaging, thus it can provide a guidance for locating of the puncture position according to a result of overlaying and merging of the elasticity image and the morphology image, accurately locating a diseased tissue, and thereby greatly improving the reliability of the aspiration biopsy.

Figure 2:
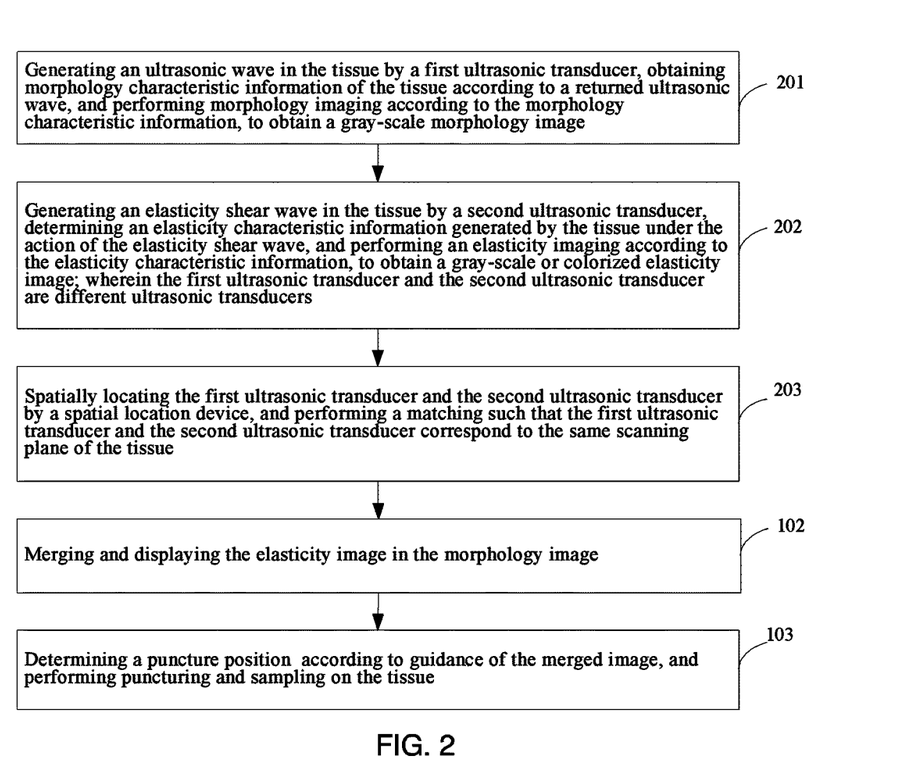
FIG. 2 is a flow chart of a second embodiment of the method for processing morphology information and elasticity information of the tissue according to the present invention.

FIG. 2 is a flow chart of the method for processing morphology information and elasticity information of the tissue according to the second embodiment of the present invention. As shown in FIG. 2, on the basis of the embodiment shown in FIG. 1, step 101 can be implemented specifically by the following steps:

step 201, generating an ultrasonic wave in the tissue by a first ultrasonic transducer, obtaining morphology characteristic information of the tissue according to a returned ultrasonic wave, and performing morphology imaging according to the morphology characteristic information to obtain a gray-scale morphology image; and step 202, generating an elasticity shear wave in the tissue by a second ultrasonic transducer, determining the elasticity characteristic information generated by the tissue under an action of the elasticity shear wave, and performing elasticity imaging according to the elasticity characteristic information to obtain a gray-scale or colorized elasticity image; wherein the first ultrasonic transducer and the second ultrasonic transducer are different ultrasonic transducers.

It should be noted that: (i) in elasticity imaging, an excitation to the tissue includes a static excitation and a dynamic excitation. The static excitation includes static or quasi-static pressing, and in this way, the second ultrasonic transducer is used to press a surface of the tissue and tissue deformation occurs. The dynamic excitation includes active and passive dynamic excitation. The active dynamic excitation includes low frequency vibration and acoustic radiation force, wherein the low frequency vibration can be achieved by the following ways: applying a low frequency instantaneous vibration to an outer surface of the tissue by a vibrator, or generating an acoustic wave on the outer surface of the tissue by a microphone; and the acoustic radiation force can be achieved by the way of focusing an ultrasonic wave emitted by the second ultrasonic transducer into inside of the tissue to generate the acoustic radiation force. The passive dynamic excitation includes respiratory movement and heartbeat. (ii) The tissue generates a responses to the applied excitation in accordance with its own mechanical characteristics. The response includes displacement, strain, shear wave velocity, etc. These parameters can be used to calculate elastic parameters of the tissue, including Young modulus, shear modulus, shear elasticity, shear viscosity, mechanical impedance, mechanical relaxation time, anisotropy, etc. Therefore the ultrasonic elasticity imaging can perform imaging for a variety of elasticity characteristic information. (iii) an ultrasonic echo signal or ultrasonic image generated by the tissue at different response moments can be collected by the second ultrasonic transducer. The ultrasonic image herein refers to a B-ultrasonic image obtained in a manner similar to that of the first ultrasonic transducer. And then the ultrasonic signals/images at different moments are processed through a processor, to obtain the elasticity characteristic information of the tissue.

In the case that the first ultrasonic transducer and the second ultrasonic transducer are different ultrasonic transducers, prior to step 102, the following step is further included:

step 203, spatially locating the first ultrasonic transducer and the second ultrasonic transducer by a spatial location device, and performing a matching such that the first ultrasonic transducer and the second ultrasonic transducer correspond to the same scanning plane of the tissue.

When the first ultrasonic transducer is used to obtain the morphology image of the tissue and the second ultrasonic transducer is used to obtain the elasticity image of the tissue, it is necessary to perform a spatial matching of the first ultrasonic transducer and the second ultrasonic transducer so that they correspond to the same scanning plane of the tissue.

Specifically, spatial locating of the two ultrasonic transducers can be realized by a spatial location device such as an electromagnetic locater/optical locater. When the spatial position of the two ultrasonic transducers correspond to the same scanning plane, a spatial matching between the morphology image and the elasticity image is realized. Electromagnetic locater/optical locater and other spatial location devices can provide a spatial locating with 6 degrees of freedom, including spatial position and spatial angle.

In addition, the above spatial location device can be used to spatially locate a puncturing device, such as a puncture needle, during the process of performing puncture sampling on the tissue by the puncturing device in accordance with a guidance of the merged image, so that the spatial position and the spatial angle of the puncturing device coincide with the spatial position and the spatial angle of the above two ultrasonic transducers with respect to the tissue, thereby achieving a more accurate puncture guidance.

Figure 3:
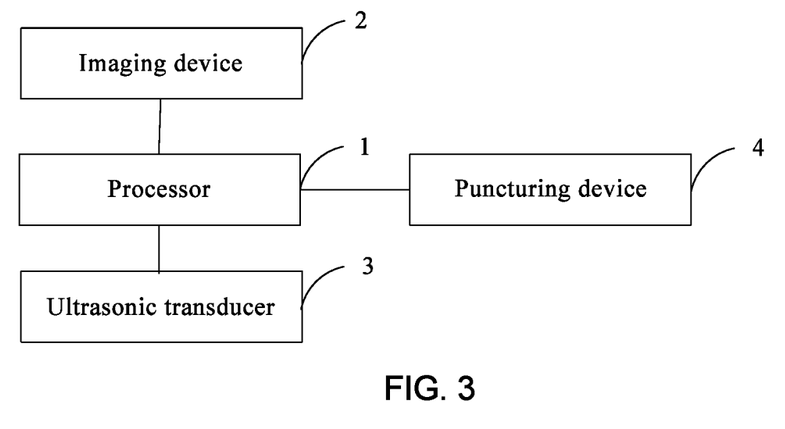
FIG. 3 is a schematic diagram of a first embodiment of the device for elasticity detection according to the present invention.

FIG. 3 is a schematic diagram of the device for elasticity detection according to a first embodiment of the present invention, As shown in FIG. 3, the device for elasticity detection includes:

a processor 1, an imaging device 2, an ultrasonic transducer 3 and a puncturing device 4;

wherein the ultrasonic transducer 3 is connected to the processor 1 and is configured to detect and obtain morphology characteristic information and elasticity characteristic information of tissue;

the imaging device 2 is connected to the processor 1 and is configured to obtain a morphology image and an elasticity image of the tissue according to the morphology characteristic information and the elasticity characteristic information, respectively, under the control of the processor 1, and merge and display the elasticity image in the morphology image; and the puncturing device 4 is connected to the processor 1 and is configured to determine a puncture position according to the guidance of the merged image and perform puncturing and sampling on the tissue.

Specifically, the number of the ultrasonic transducer is one or two.

The device for elasticity detection of the present embodiment can be configured to carry out the technical solution of the method embodiment shown in FIG. 1, and their implementation principles and technical effects are similar, which will not be repeated here.

Figure 4:
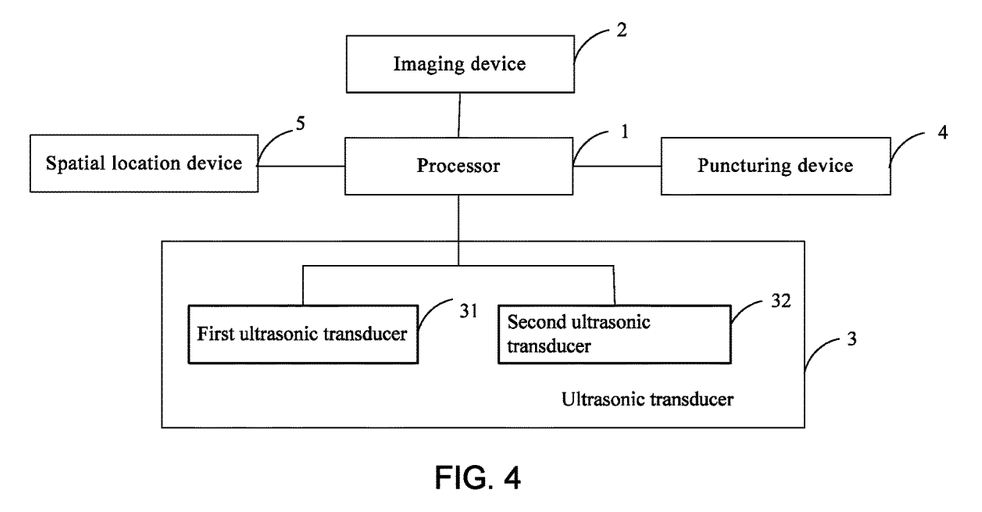
FIG. 4 is a schematic diagram of a second embodiment of the device for elasticity detection according to the present invention.

FIG. 4 is a schematic diagram of the device for elasticity detection according to a second embodiment of the present invention. As shown in FIG. 4, on the basis of the embodiment shown in FIG. 3, optionally, the ultrasonic transducer 3 includes a first ultrasonic transducer 31 and a second ultrasonic transducer 32, and the first ultrasonic transducer 31 and the second ultrasonic transducer 32 are connected to the processor 1;

the first ultrasonic transducer 31 is configured to generate an ultrasonic wave in the tissue and obtain the morphology characteristic information according to a returned ultrasonic wave;

the processor 1 is further configured to control the imaging device to perform gray-scale imaging according to the morphology characteristic information, to obtain a gray-scale morphology image;

the second ultrasonic transducer 32 is configured to generate an elasticity shear wave in the tissue and determine the elasticity characteristic information generated by the tissue under an action of the elasticity shear wave; and the processor 1 is further configured to control the imaging device to perform an elasticity imaging according to the elasticity characteristic information, to obtain a gray-scale/colorized elasticity image.

Further, the device for elasticity detection further includes a spatial location device 5 connected to the processor 1.

The spatial location device 5 is configured to spatially locate the first ultrasonic transducer 31 and the second ultrasonic transducer 32, and perform a matching such that the first ultrasonic transducer 31 and the second ultrasonic transducer 32 correspond to the same scanning plane of the tissue.

Specifically, the spatial location device 5 includes an electromagnetic locater or an optical locater.

In this case, in the gray-scale elasticity image, different gray-scales represent elasticity characteristic information corresponding to different positions of the tissue; and in the colorized elasticity image, different colors represent elasticity characteristic information corresponding to different positions of the tissue.

In the gray-scale morphology image, different gray-scales represent morphology characteristic information corresponding to different positions of the tissue.

Specifically, the imaging device 2 is configured to:

display in the gray-scale morphology image the elasticity characteristic information represented by the different gray-scales or the different colors in the gray-scale or colorized elasticity image.

The device for elasticity detection of the present embodiment can be configured to carry out the technical solutions of the method embodiment shown in FIG. 2, and their implementation principles and technical effects are similar, which will not be repeated here.

It will be appreciated by those of ordinary skill in the art that all or part of the steps for implementing the method embodiments described above may be accomplished by a program instruction related hardware, the program may be stored in a computer-readable storage medium. When the program is executed, it executes the steps included in the method embodiments described above; and the aforementioned storage medium includes: a variety of media that can store program codes, such as a ROM, a RAM, a magnetic disk, or an optical disk.

Finally, it should be understood that the above embodiments are merely to illustrate technical solutions of the present invention and are not to be construed to be limiting; although the present invention has been described in detail with reference to the foregoing embodiments, it should be understood by those skilled in the art that modifications may be made to the technical solutions described in the foregoing embodiments or equivalent replacements may be made to some or all of the technical features in these embodiments. These modifications and replacements do not render the essence of the corresponding technical solutions departing from the scope of the technical solutions of the embodiments in the present invention.

What is claimed is:

1. A method for processing morphology information and elasticity information of a tissue, comprising:

obtaining a morphology image and an elasticity image of the tissue, wherein the morphology image includes morphology characteristic information of the tissue, and the elasticity image includes elasticity characteristic information of the tissue;

merging and displaying the elasticity image in the morphology image for generating one merged image simultaneously displaying the morphology image and the elasticity image; and determining a puncture position according to a guidance of the one merged image;

wherein the obtaining a morphology image and an elasticity image of the tissue comprises:

spatially locating a first ultrasonic transducer and a second ultrasonic transducer by a spatial location device, wherein the spatial location device comprises an electromagnetic locater or an optical locater, and performing a matching such that the first ultrasonic transducer and the second ultrasonic transducer correspond to a same scanning plane of the tissue, wherein the first ultrasonic transducer and the second ultrasonic transducer are different ultrasonic transducers;

generating an ultrasonic wave in the tissue by the first ultrasonic transducer, obtaining the morphology characteristic information according to a returned ultrasonic wave, and performing morphology imaging according to the morphology characteristic information to obtain a gray-scale morphology image;

generating an elasticity shear wave in the tissue by the second ultrasonic transducer, determining the elasticity characteristic information generated by the tissue under an action of the elasticity shear wave, and performing elasticity imaging according to the elasticity characteristic information to obtain a gray-scale or colorized elasticity image;

wherein in the gray-scale elasticity image, different gray-scales represent elasticity characteristic information corresponding to different positions of the tissue; and in the colorized elasticity image, different colors represent elasticity characteristic information corresponding to different positions of the tissue; and in the gray-scale morphology image, different gray-scales represent morphology characteristic information corresponding to different positions of the tissue;

wherein the merging and displaying the elasticity image in the morphology image comprises:

displaying in the gray-scale morphology image the elasticity characteristic information represented by the different gray-scales or the different colors in the gray-scale or colorized elasticity image;

wherein the spatial location device is used to spatially locate a puncturing device during a process of performing puncture sampling on the tissue by the puncturing device according to the guidance of the one merged image such that a spatial position and a spatial angle of the puncturing device and a spatial position and a spatial angle of the first ultrasonic transducer and the second ultrasonic transducer with respect to the tissue are relative to the same scanning plane, wherein the puncturing device is a puncture needle.

2. A device for elasticity detection, comprising an ultrasonic transducer, a puncturing device, a processor and a memory storing instructions thereon, wherein the ultrasonic transducer is connected to the processor and is configured to detect and obtain morphology characteristic information and elasticity characteristic information of a tissue, the processor when executing the instructions, being configured to:
  obtain a morphology image and an elasticity image of the tissue according to the morphology characteristic information and the elasticity characteristic information, respectively, and merge and display the elasticity image in the morphology image for generating one merged image simultaneously displaying the morphology image and the elasticity image; and
  the puncturing device is connected to the processor, and is configured to determine a puncture position according to a guidance of the one merged image and perform a puncturing and sampling on the tissue, wherein the puncturing device is a puncture needle;
  wherein the ultrasonic transducer comprises a first ultrasonic transducer and a second ultrasonic transducer, and the first ultrasonic transducer and the second ultrasonic transducer are connected to the processor;
  the first ultrasonic transducer is configured to generate an ultrasonic wave in the tissue and obtain the morphology characteristic information according to a returned ultrasonic wave;
  the processor is further configured to perform morphology imaging according to the morphology characteristic information to obtain a gray-scale morphology image;
  the second ultrasonic transducer is configured to generate an elasticity shear wave in the tissue and determine the elasticity characteristic information generated by the tissue under the action of the elasticity shear wave; and
  the processor is further configured to perform an elasticity imaging according to the elasticity characteristic information, to obtain a gray-scale or colorized elasticity image;
    wherein in the gray-scale elasticity image, different gray-scales represent elasticity characteristic information corresponding to different positions of the tissue; and in the colorized elasticity image, different colors represent elasticity characteristic information corresponding to different positions of the tissue; and
    in the gray-scale morphology image, different gray-scales represent morphology characteristic information corresponding to different positions of the tissue;
  wherein the processor is further configured to:
  display in the gray-scale morphology image the elasticity characteristic information represented by the different gray-scales or the different colors in the gray-scale or colorized elasticity image;
  wherein the processor is further configured to:
  spatially locate the first ultrasonic transducer and the second ultrasonic transducer, and perform a matching such that the first ultrasonic transducer and the second ultrasonic transducer correspond to a same scanning plane of the tissue, wherein the first ultrasonic transducer and the second ultrasonic transducer are different ultrasonic transducers; and spatially locate the puncturing device during a process of performing puncture sampling on the tissue by the puncturing device according to the guidance of the one merged image such that a spatial position and a spatial angle of the puncturing device and a spatial position and a spatial angle of the first ultrasonic transducer and the second ultrasonic transducer with respect to the tissue are relative to the same scanning plane.

3. The device for elasticity detection according to claim 2, wherein the number of the ultrasonic transducers is one or two.

4. The method according to claim 1, wherein the obtaining the morphology characteristic information according to a returned ultrasonic wave, and performing morphology imaging according to the morphology characteristic information to obtain a gray-scale morphology image, comprises:
  transforming, by the first ultrasonic transducer, the returned ultrasonic wave into electrical signals using an inverse piezoelectric effect obtain the morphology characteristic information, and performing morphology imaging according to the morphology characteristic information with AD sampling, beam forming, envelope detection or logarithmic compression to obtain the gray-scale morphology image.

5. The method according to claim 1, wherein the generating an elasticity shear wave in the tissue by the second ultrasonic transducer, determining the elasticity characteristic information generated by the tissue under an action of the elasticity shear wave, comprises:
  generating a first elasticity shear wave in the tissue by the second ultrasonic transducer to obtain a first signal;
  applying an active dynamic excitation on the tissue;
  generating a second elasticity shear wave in the tissue by the second ultrasonic transducer to obtain a second signal; and
  detecting time shift, frequency shift, or phase shift according to the first signal and the second signal to obtain the elasticity characteristic information.

6. The method according to claim 5, wherein the active dynamic excitation comprises low frequency vibration and acoustic radiation force.

7. The method according to claim 6, wherein the low frequency vibration is applied to an outer surface of the tissue by at least one of a vibrator or a microphone.

8. The method according to claim 6, wherein the acoustic radiation force is applied by focusing an ultrasonic wave emitted by the second ultrasonic transducer into inside of the tissue.

9. The device for elasticity detection according to claim 2, wherein the first ultrasonic transducer is further configured transform the returned ultrasonic wave into electrical signals using an inverse piezoelectric effect obtain the morphology characteristic information; and
  the processor is further configured to perform morphology imaging according to the morphology characteristic information with AD sampling, beam forming, envelope detection or logarithmic compression to obtain the gray-scale morphology image.

10. The device for elasticity detection according to claim 2, wherein the device further comprises an active dynamic exciter;
  the second ultrasonic transducer is further configured to generate a first elasticity shear wave in the tissue to obtain a first signal;
  the active dynamic exciter is configured to apply an active dynamic excitation on the tissue;

the second ultrasonic transducer is further configured to generate a second elasticity shear wave in the tissue to obtain a second signal; and the processor is further configured to detect time shift, frequency shift, or phase shift according to the first signal and the second signal to obtain the elasticity characteristic information.

11. The device for elasticity detection according to claim 10, wherein the active dynamic excitation comprises low frequency vibration and acoustic radiation force.

12. The device for elasticity detection according to claim 11, wherein the acoustic radiation force is applied by focusing an ultrasonic wave emitted by the second ultrasonic transducer into inside of the tissue.

13. The device for elasticity detection according to claim 11, wherein the active dynamic exciter comprises at least one of a vibrator, a microphone and the second ultrasonic transducer.

14. The device for elasticity detection according to claim 13, wherein the low frequency vibration is applied to an outer surface of the tissue by at least one of the vibrator and the microphone.

* * * * *